US00PP08907P

United States Patent [19]

Drewlow

[11] Patent Number: Plant 8,907

[45] Date of Patent: Sep. 20, 1994

[54] IMPATIENS PLANT NAMED CANON

[75] Inventor: Lyndon W. Drewlow, Ashtabula, Ohio

[73] Assignee: Mikkelsens, Inc., Ashtabula, Ohio

[21] Appl. No.: 163,767

[22] Filed: Dec. 9, 1993

[51] Int. Cl.[5] ..... A01H 5/00
[52] U.S. Cl. ..... Plt./87.6
[58] Field of Search ..... Plt. 87.6

*Primary Examiner*—James R. Feyrer
*Attorney, Agent, or Firm*—Foley & Lardner

[57] ABSTRACT

A new and distinct cultivar of Impatiens plant named Canon, characterized by its light pink to white relatively small diameter double flowers which have 10 petals, solid deep green leaves with no variegation, highly self-branching and floriferous habits, yellow-green flower spur, flowering entirely above leaf canopy, tolerance to both high and cool temperatures, and its adaptability to be grown in 10 cm up to 15–25 cm containers.

1 Drawing Sheet

The present invention relates to a new and distinctive cultivar of Impatiens plant, botanically known as Impatiens, commercially known as New Guinea Impatiens, and known by the cultivar name Canon.

The new culture was developed in a controlled breeding program conducted by the inventor Lyndon W. Drewlow in Ashtabula, Ohio. Canon was created by crossing Mikkelsen Seedling No. 90-132-2 (seed parent) with Mikkelsen Seedling No. 90-169-2 (pollen parent). Both parents are proprietary cultivars used in the breeding program.

Asexual reproduction by terminal or stem cuttings carried out by or under the supervision of the inventor at Ashtabula, Ohio has shown that the unique features of this new Impatiens are stabilized and are reproduced true to type in successive propagations.

The following combination of characteristics distinguish the new Impatiens from both its parent varieties and other cultivated Impatiens of this type known and used in the floriculture industry. The description includes reference to comparison cultivars Dawn, disclosed in U.S. Plant Pat. No. 5,775, and Sonata, disclosed in a pending application of the inventor.

1. Canon is a representative of an entirely new class of New Guinea Impatiens that have ten flower petals, double the number of petals of single flower types such as Dawn with five petals. Sonata is another cultivar in the double flowered group.

2. Canon is light pink in flower color (56C) while Dawn is salmon pink (48C) and Sonata is salmon orange (34B to 34C).

3. Canon has a smaller diameter flower at 4.5 to 5.0 cm than either Dawn at 5.0 to 6.0 cm or Sonata at 5.5 to 6.0 cm.

4. Canon has a 4.0 cm yellow green flower spur, while Dawn has a 3.0 to 3.25 cm long salmon pink spur and Sonata a 4.5 cm long light reddish purple flower spur.

5. Flower pedicels of Canon are 2.5 to 3.0 cm long and green in color, while the pedicels of Dawn are 3.5 to 4.0 cm long and have a reddish tint. Sonata has green pedicels 3.0 to 3.5 cm long.

6. The leaves of Canon are 8–9 cm long and 3.0–3.5 cm wide, larger than the leaves of Dawn which are 4 to 5 cm long and 2.25 to 2.5 cm wide, and smaller than the leaves of Sonata which are 10 to 11 cm long and 3.5 to 4.0 cm wide.

7. Canon has solid green leaves as does Sonata, while Dawn has a green leaf with cream variegation around the midrib near the basal end of the leaf.

8. There are 5 to 6 leaves in a whorl on Canon, with Dawn having 5 leaves in a whorl and Sonata having 6 to 7 leaves in a whorl.

9. Canon is 3 to 5 days later to bloom than Dawn as it takes the double flowers longer to develop and open. Sonata is similar in bloom date to Canon.

10. Both Canon and Sonata are more self-branched than Dawn. Canon is 20 to 22 cm in height with Dawn shorter at 16 to 18 cm in height and Sonata taller at 24 to 26 cm.

11. Canon has a white anther hood while both Dawn and Sonata have a reddish tint in anther hood.

In the photographic drawings, the color photo at the top illustrates in perspective view the overall appearance of Canon, with the colors being as true as it is reasonably possible to obtain in a color reproduction of this type. The color photo was taken on Sept. 24, 1993 under natural light under 40% saran in a shaded glass greenhouse in Ashtabula, Ohio on a sunny day. The black and white photo on the bottom shows three (3) views of a typical flower of the new cultivar.

The following is a detailed description of Canon, based on plants produced in greenhouses in Ashtabula, Ohio during the summer season of the year. Plants were grown in 15 cm pots and measurements were taken 18 weeks after rooted cuttings were planted. Height measurements were taken from the soil line of the container. The plants were grown at 65°–68° F. night temperatures under 3000–4000 foot candles of light, and 250 ppm nitrogen, 75 ppm potassium, and 250 ppm phosphorous nutritional levels, with trace elements added. The habit of grown, foliage coloration, leaf variegation, size of leaves and flower size will be influenced by nutritional and environmental conditions, without, however, any variance in the genotype.

Color references are made to The Royal Horticultural Society Color Chart except where general terms of ordinary dictionary significance are used.

Parentage: A controlled cross between female parent Mikkelsen Seedling No. 90-132-2 and Mikkelsen Seedling 90-169-2 as male parent.

Propagation:

(A) *Type cutting.*—Stem tip 15 mm long will develop 4 to 5 cm long in 18 to 21 days.

(B) *Time to root.*—8–10 days at 23° C. summer; 10–12 days at 20° winter.

(C) *Rooting habit.*—Heavy, fibrous.

Plant description:

(A) *Form and habit of growth.*—Highly self-branched, mounded, intermediate in height, flowers over leaf canopy; continuous flowering; vigorous growing herb.

(B) *Foliage.*—Deep green with yellow green mid-rib and petiole, no variegation, petiole very short at 5 mm or less in length. (1) Size: 8 to 9 cm long and 3.0 to 3.5 cm wide for average mature leaf. (2) Shape: Lanceolate with acuminate apex and acute base. (3) Texture: Both upper and lower surfaces are glabrous. (4) Margin: Finely serrated with fine ciliate. (5) Color: Young foliage, top side is 146A; under side is 146B; mature foliage, top side is 147A; under side is 147B. (6) Veination: Pinnate, green in color.

Flowering description:

(A) *Flowering habit.*—Flowering continuously from leaf whorl in a progressively orderly manner with one flower per leaf axil. When the last flower in a leaf whorl opens the first flower in the leaf whorl above starts to open. It takes 5 to 7 days for a mature bud to fully open and the flower may last two weeks or longer depending on environment.

(B) *Natural flowering season.*—Indeterminant and continuous; quantity of flowering increases with increasing levels of light.

(C) *Flower buds.*—Ellipsoidal, flowers perfect; light yellow green 4.0 cm long spur with green tip on mature bud, with throat behind the ovary and originating from the major sepal.

(D) *Flowers borne.*—On individual green pedicels 2.5 to 3.0 cm long from whorl of 5 to 6 leaves, flowering progressively around the whorl as buds and leaves develop. One flower per leaf axil is normal.

(E) *Quantity of flowers.*—Very floriferous because of high degree of self-branching of plant, long-lasting flowers and full appearance of double flowers.

(F) *Diameter of flower.*—4.5 to 5.0 cm.

(G) *Petals.*—(1) Shape: Heart, two keel petals of bottom whorl of petals are the largest. (2) Color: Top side in summer when opening is 55B in certain areas of petal, with large areas of 56C and 155D around eye of flower; fading to mostly 56C and 155D with only a trace of 55B; under side is 56C. (3) Number of petals: Ten. (4) Type of petals: There is only one true standard petal in lower whorl. No petal in upper whorl is like a standard petal. There are two sets of wing petals, with the upper whorl pair the largest. The lower whorl has two normal keel petals and upper whorl has two normal keep petals plus a third keel-like petal.

(H) *Reproductive organs.*—(1) Stamens: Five (5) in number. (a) Anther: Hooded shape; color is white. (b) Pollen color: Cream. (2) Pistils: (a) Stigma shape: Five (5), segmented column; color is greenish white. (b) Style color: Greenish white. (c) Ovaries: Five (5) in number; size is 3 mm when mature; color is green.

Disease resistance: No significant insect or disease problems to date.

OTHER IMPORTANT CHARACTERISTICS

1. Self-branching characteristic, and medium height and mounded growth habit make Canon suitable for 10 cm pot production, but Canon is vigorous enough for 15 and 25 cm pot production as well.
2. Canon can withstand both high temperatures and sunlight as well as low temperatures (40° to 50° F.). Thus, growing season outdoors for Canon can be extended as well as the location where it can be planted.
3. The 10 flower petals result in a fuller looking flower as compared to the normal 5 petals. A double flowered plant with the same number of flowers as a single flowered plant will appear substantially more colorful.

I claim:

1. A new and distinct cultivar of Impatiens plant named Canon, as illustrated and described.

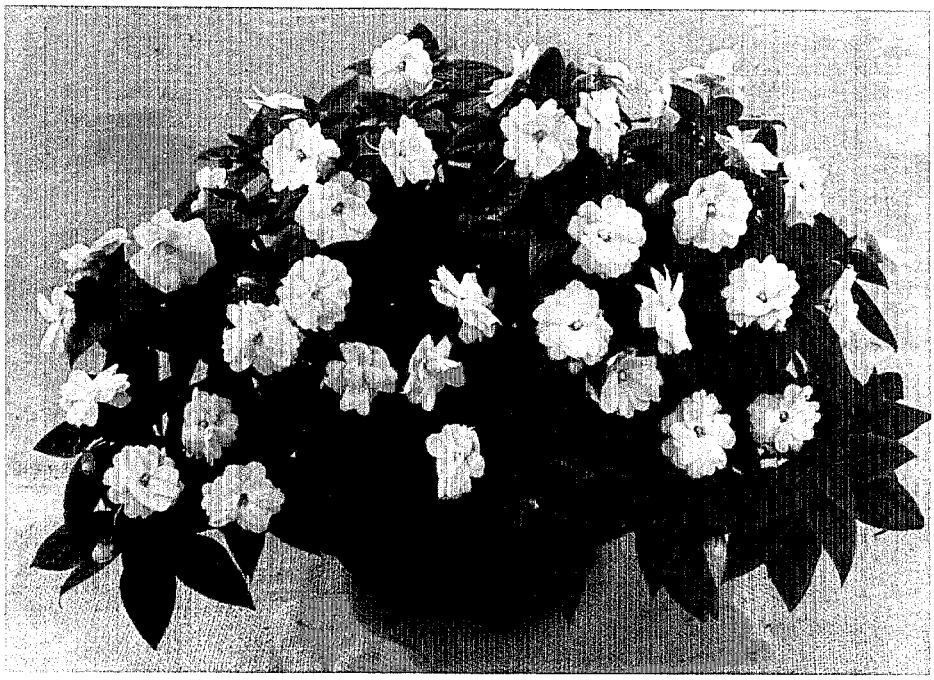

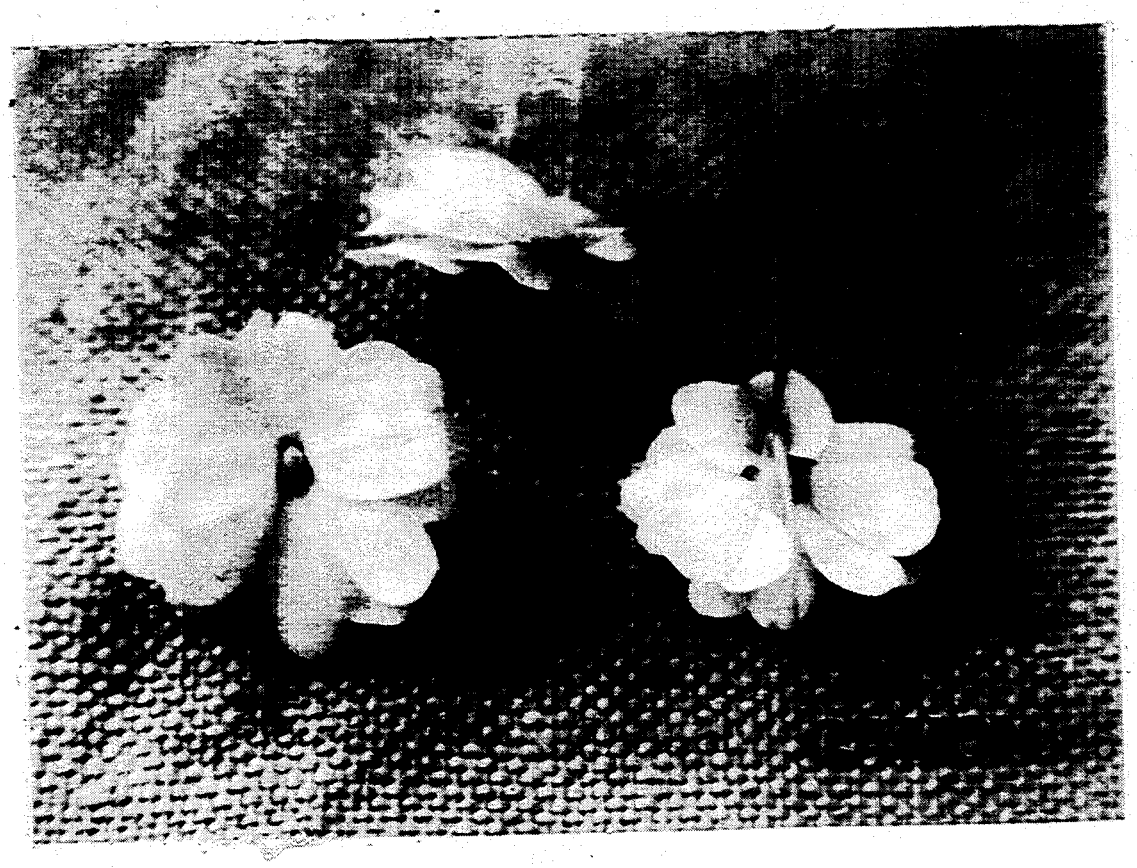

* * * * *